United States Patent [19]

Savaides et al.

[11] Patent Number: 5,617,883
[45] Date of Patent: Apr. 8, 1997

[54] REDUCING AGENTS FOR PERMANENT WAVING OF HAIR

[75] Inventors: Andrew Savaides, Norwalk; Thomas M. Schultz, Ridgefield; Sanae Kubo, Darien, all of Conn.; Edward Borish, Mahwah, N.J.

[73] Assignee: Shiseido Co., Ltd., Tokyo, Japan

[21] Appl. No.: 305,574

[22] Filed: Sep. 14, 1994

[51] Int. Cl.$^6$ .............................. A45D 7/06; A61K 7/09
[52] U.S. Cl. ........................................ 132/205; 424/70.2
[58] Field of Search .................. 132/203, 204, 132/205, 206, 209; 424/70.2

[56] References Cited

U.S. PATENT DOCUMENTS

| | | | |
|---|---|---|---|
| 3,768,490 | 10/1973 | Kalopissis et al. | 132/203 |
| 3,840,656 | 10/1974 | Kalopissis et al. | 424/47 |
| 4,859,459 | 8/1989 | Greiche et al. | 424/71 |
| 5,085,860 | 2/1992 | Junino et al. | 424/72 |
| 5,241,973 | 9/1993 | Salce et al. | 132/205 |
| 5,401,497 | 3/1995 | Rose | 424/70.2 |

*Primary Examiner*—Robert P. Swiatek
*Assistant Examiner*—Yvonne R. Abbott
*Attorney, Agent, or Firm*—Melvin I. Stoltz

[57] ABSTRACT

A highly effective permanent waving lotion is attained by employing one compound selected from the group consisting of glyceryl monothiopropionate, glyceryl thiolactate, and combinations of glyceryl monothiopropionate and glyceryl thiolactate as the sole reducing agent. In accordance with this invention, the reducing agent is employed either independently in an aqueous solution or in association with desired additives for imparting additional benefits to the permanently waved hair. Preferably, the reducing agents of the present invention are employed in a permanent waving lotion having a pH ranging between about 6.0 and 9.5. In this way, processing time is reduced and long lasting permanently waved hair is attained with substantially less malodor being produced.

15 Claims, No Drawings

REDUCING AGENTS FOR PERMANENT WAVING OF HAIR

TECHNICAL FIELD

This invention relates to the art of permanently waving hair, and more particularly, to new compounds which can be employed as reducing agents to provide substantially increased, long-lasting, durable permanently waved hair while also substantially reducing the malodor typically associated with permanent waving.

BACKGROUND ART

The permanent waving of hair is a well established and well developed art in which substantial attention has been directed to improve the present level of technology. Although substantial changes have occurred throughout the last decades, various problems continue to plague the industry in spite of numerous attempts to reduce or eliminate these problems.

In order to best understand the present state of the art and the problems existing therein, it is important to reiterate that hair fibers are composed of a unique protein called "keratin" which is distinguished by the fact that it contains a very significant amount of an amine acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S—S) to give keratin protein (K—S—S—K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free —SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

  (i)

  (ii)

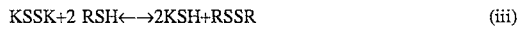  (iii)

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

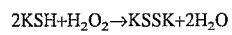

The most commonly used reducing agents employed in the permanent deformation of hair keratin are salts and esters of thioglycolic acid. Other less commonly used reducing agents include cysteine, cysteamine, thiolactic acid and their derivatives. These reducing agents are very effective in the reduction of disulfide bonds and under certain conditions can reduce more than 50% of the keratin cystine bonds.

Although effective in providing excellent reducing capabilities, the above mercaptans and their corresponding derivatives possess problems that are difficult to control. One of the disadvantages is the emission of malodor, which is very common with sulfur compounds. This characteristic creates discomfort to both the stylist and the individual who undergoes permanent waving. Therefore, fragrances are used with reducing agents to mask unpleasant sulfur odors. Other disadvantages include the irreversible fiber alteration as made evident by increased fiber porosity and decreased tensile properties.

Much efforts have been expended in attempts to minimize these attributes. These include pretreatments, barriers which decrease the rate of diffusion, reduction of the mercaptan concentration and/or the pH of the reducing agents, and duration of reduction time. Many of these pretreatments yield other undesirable characteristics such as oily, greasy, and dirty feeling of the hair fiber.

Furthermore, in the art of permanent waving, there is much trial and error, with the hair being over-processed, in some instances. The characteristics of over-processing are raspy feel to the hair or a loss of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care.

In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical changes in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Therefore, it is a principal object of the present invention to provide a composition for permanently waving hair fibers which is capable of imparting to the head of hair a durable, long-lasting permanent hair set retention, while substantially eliminating the malodor typically resulting from the waving process.

Another object of the present invention is to provide a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition having the characteristic features described above which is capable of imparting a long-lasting permanent wave or setting property to the hair, while substantially reducing hair damage caused during the reduction and oxidation processes.

A further object of the present invention is to provide a permanent wave composition having the characteristic features described above which is capable of improving the elastic and tensile properties of the hair fibers.

Other and more specific objects will in part be obvious and will in part appear hereinafter.

DETAILED DESCRIPTION

By employing the present invention, the prior art limitations and difficulties have been overcome and a long-lasting, permanently waved head of hair is attained using a new permanent waving agent which is capable of being effectively employed at higher pH levels with substantially less malodor than is typically produced by prior art agents. In addition, the permanent waving agents of the present invention impart long lasting hair conditioning and enhanced physical properties to the hair fibers, such as shine, luster, softness, manageability and hair thickness.

In accordance with the present invention, the desirable and previously unattainable enhanced characteristics are realized by employing as the sole reducing agent at least one compound selected from the group consisting of glyceryl monothiopropionate (GMTP), glyceryl thiolactate (GMTL), and combinations of glyceryl monothiopropionate and glyceryl thiolactate. As detailed herein, the glyceryl monothiopropionate and glyceryl thiolactate are employed as the sole reducing agent, either independently, or in combination, in an aqueous solution or, if desired, in association with desired additives for imparting additional benefits to the resulting permanently waved hair. Such additives include protein hydrolysates, conditioning agents, fragrances, ionic or non-ionic wetting agents, chelating agents, such as EDTA, and penetrating agents, such as phenoxyethanol, urea, 2,3 hexanediol and phytantriol.

In addition, oxidizing agents may be incorporated into the reducing lotion to produce an exothermic reaction during the application and use of the reducing lotion. Preferably, the oxidizing agents are selected from the group consisting of hydrogen peroxide and water soluble salts of bromates.

Glyceryl monothiopropionate (GMTP) is also known as 3-mercaptopropyl glycerate and glyceryl-3 mercaptopropionate. This compound is identified by CAS No. 111873-04-2. Glyceryl thiolactate (GMTL) is also known as glyceryl-2-mercaptopropionate.

Glyceryl monothiopropionate and glyceryl thiolactate have both been found to be extremely effective in breaking the disulfide bonds within the hair fiber in the manner which enables permanent waving of the hair fibers to be attained. It has also been found that by employing these compounds as the sole reducing agent, enhanced physical properties are attained and substantially less malodor is produced. This reduction in the malodor typically associated with conventional reducing agents is a significant advance enjoyed by both the beautician as well as the customer.

It has been found that optimum efficacy is attained by having the pH of the aqueous reducing agent ranging between about 6.0 and 9.5. Generally, preferred results are obtained with the pH ranging between about 8 and 9.2. These higher pH levels are desirable since processing time is reduced. Furthermore, permanent waving of more resistant fibers is also realized.

In order to attain the desired pH level an alkaline agent is employed in the aqueous solution in a sufficient quantity to achieve the desired pH level. Preferably, the alkaline agent is selected from the group consisting of ammonia, ammonium hydroxide, monoethanolamine, guanidine, diethanolamine, triethanolamine, ammonium carbonate, and bicarbonate, and is used in admixture with the reducing agent to form a pH balancing solution capable of controlling the pH of the waving lotion.

As discussed above, a permanent waving lotion can be prepared using the reducing agent of the present invention in combination with other additives for imparting additional benefits to the resulting permanently waved hair. In preparing a permanent waving lotion of this nature, an aqueous solution containing any desired penetrating agents, chelating agents, wetting agents, fragrances, and conditioning agents is separately prepared. Then, immediately prior to application to the hair, the conditioning agents are intermixed with the aqueous solution of the reducing agent and the pH adjusted using a desired alkaline agent, to produce a pH ranging between about 6.0 and 9.5. The resulting permanent waving and reducing lotion is then ready for immediate use on any desired head of hair.

In addition, if an oxidizing agent is employed to achieve an exothermic reaction within the reducing lotion, the oxidizing agent is prepared separately and added to the reducing agent along with conditioning agents immediately prior to use. In this way, the desired exothermic reaction occurs while the reducing lotion is on the hair.

In Table I, an overall general formulation for a permanent wave reducing lotion made in accordance with the present invention is provided. By referring to this formulation, the various desired ingredients and quantity of each ingredient on a percent by weight basis, based upon the entire weight of the overall composition, is detailed.

TABLE I

| Permanent Wave Reducing Lotion Composition | |
| --- | --- |
| Ingredient | % by Weight |
| GMTP or GMTL | 5%–50% |
| Ionic or Nonionic Detergent | 2%–6% |
| Fragrance | 0.5%–2% |
| Ammonium Chloride | 1%–3% |
| Penetrating Agent | 2%–5% |
| Alkaline Agent | adjust pH as desired |
| Oxidizing Agent | 0%–10% |
| Deionized Water | q.s. to 100% |

In employing the present invention, a generally conventional application process is employed, using either an aqueous solution of the reducing agent of this invention or a permanent wave reducing lotion, as detailed above. The reducing agent or permanent wave reducing lotion is applied directly to freshly shampooed and moistened hair which has been previously rolled on rollers. The hair fibers are thoroughly wetted by the reducing agent or the permanent wave reducing lotion, which is allowed to remain on the moistened hair for between 10 and 60 minutes. Although this range has been found to be effective, the reducing agent or lotion is preferably allowed to remain on the hair for between about 5 and 30 minutes. If desired, the reaction may be accelerated by applying heat to the hair. However, it has been found that heat is usually not required. If heat is employed, any conventional temperature may be used, however, a temperature of about 50° C. has been found to be most effective.

Once the desired reaction time has been achieved, the hair is rinsed with water and blotted to remove excess moisture. Then, the hair is neutralized or oxidized with a solution which incorporates one or more agents selected from the group consisting of acidic hydrogen peroxide, alkaline bromate, and sodium chlorite. Preferably, the oxidizing solution is applied to the hair and allowed to remain on the hair for between about 2 and 10 minutes. However, alternate time ranges can be employed without departing from the scope of this invention. Finally, the hair tresses are rinsed with running water for 2 minutes, unwound from the rod and allowed to dry.

If desired, alkaline agents may be incorporated into the neutralizer in order to attain an exothermic reaction. Preferably, the alkaline agent comprises one or more water soluble salts selected from the group consisting of sulfites, and bisulfites.

By employing the present invention, a substantially improved and enhanced permanently waved head of hair is attained. In addition, the present invention also provides physical characteristics, such as gloss, combability, and softness, while also substantially increasing curl retention or hair set permanency. Furthermore, and of particular importance, is the substantial elimination of malodor which is typically associated with permanently waved hair. As a result, the present invention is capable of eliminating most of the prior art problems, while providing a highly effective reducing lotion for permanently waving heads of hair which is employable in comfort, without causing exposure to offensive odors.

The invention accordingly comprises the several steps and the relation of one or more of such steps with respect to each of the others, and the composition possessing the features, properties, and relation of components, all as exemplified herein, with the scope of the invention being indicated in the claims.

BEST MODE FOR CARRYING OUT THE INVENTION

In order to substantiate the efficacy of glyceryl monothiopropionate and glyceryl thiolactate as reducing agents, the following examples are presented. In this disclosure, the universal applicability of the present invention is fully detailed, along with the ability of the composition to permanently wave hair with substantially improved, long-lasting, physical enhancements and characteristics being attained thereby. However, it is to be understood that these examples are intended as a teaching of the best mode for carrying out the present invention and are not intended to limit, in any manner, the breadth of this discovery.

In addition, the examples detailed herein clearly demonstrate that although either glyceryl monothiopropionate or glyceryl thiolactate can be effectively employed as the sole reducing agent in a permanent waving lotion, the use of glyceryl monothiopropionate is preferred in view of its superior performance. The ability of glyceryl monothiopropionate to provide an improved long-lasting permanent wave at substantially higher pH levels than ordinarily employed for most conventional acid waves, while also substantially reducing malodor associated with permanent waving, is demonstrated in the examples detailed herein.

In order to prove the efficacy of the present invention, numerous hair tresses were tested by being permanently waved using the compounds of the present invention as the sole reducing agent and comparing the results to hair tresses permanently waved with conventional reducing agents. In order to provide a standard by which the waving efficiency of the reducing agents can be objectively evaluated, the "Deficiency in Wave Tightness" (DIWT) was determined for each sample and compared.

In determining the Deficiency in Wave Tightness (DIWT), the Test Tube Test Curl (TTTC) procedure was used for each reducing agent at each pH level. Twelve fleshly shampooed human hair fibers were knotted at the root end and cut to a length of 3.5 inches from the knot. The bundle is immersed in water and then wound around an aluminum mandrel having a diameter of 6.5 mm., and then immersed into 15 ml of the reducing solution at a constant temperature of about 37° C., for 10 minutes. Once completed, the hair fibers were rinsed with running water for two minutes.

After rinsing, the hair fibers were immersed in 15 ml of the neutralizer and allowed to stand for three minutes. Then, the hair fibers were rinsed with running water for two minutes. Following the rinsing, the hair fibers were unwound from the aluminum mandrel and the obtained coil is immersed in water. Thereafter, both the length of the hair fiber and diameter of the resulting hair coil were recorded.

In permanently waving hair using this type of reducing agent, an acceptable curl has a curl diameter (D) ranging between about 7.00 and 10.40 mm, and a coil length (L) ranging between about 27 and 37 mm. Using this data, the Deficiency in Wave Tightness (DIWT) is determined, which represents the overall waving efficiency of the reducing agent. In general, acceptable DIWT results range between about 8 and 60.00. The "Deficiency in Wave Tightness" or DIWT is calculated as follows:

$$DIWT = \frac{\text{diameter of hair coil (mm)} - \text{diameter of mandrel (mm)}}{\text{diameter of mandrel (mm)}} \times 100$$

EXAMPLE 1

In order to demonstrate both the efficacy and the improved results obtained by employing the reducing agent of the present invention, numerous tests were conducted using glyceryl monothiopropionate and glyceryl thiolactate as the sole reducing agent at different pH levels. Similar tests were also conducted using conventional reducing agents.

In the first series of tests, the hair samples consisted of untreated, level 6 Brown human hair obtained from DeMeo Brothers of New York, N.Y. In conducting these tests, in the manner detailed above, the hair fibers were processed with a 1.0N aqueous solution of the reducing agent. The pH level was maintained by employing ammonia and also employing monoethanolamine in a separate series of experiments using the same conditions and procedures. As discussed above, the use of alkalizing agents such as ammonia, ammonium hydroxide, monoethanolamine, guanidine, diethanolamine, triethanolamine, ammonium carbonate, bicarbonate and the like can be used in admixture to form a pH balancing solution capable of controlling the pH of the waving lotion.

Following the removal of the reducing lotion by rinsing, a 2.2% hydrogen peroxide solution was employed for five minutes. The pH of the neutralizer was adjusted with phosphoric acid to be 3.5.

In Tables II and III, the test results obtained are provided with the diameter of the resulting curl (D) and the length of the curl (L) being given for the varying pH of each hair keratin reducing agent. In addition, in Tables IV and V, the deficiency in wave tightness (DIWT) for each hair keratin reducing agent (HKRA) is provided as a function of pH. In Tables II and IV, ammonia was employed as the alkalizing agent, while monoethanolamine was used in the results shows in Table III and V.

TABLE II

Effect of pH of Hair Keratin Reducing Agent (HKRA) On Curl Tightness

| | pH | | | | | | | | | | | | | |
|---|---|---|---|---|---|---|---|---|---|---|---|---|---|---|
| | 7.0 | | 7.5 | | 8.0 | | 8.5 | | 9.0 | | 9.5 | | 10.0 | |
| HKRA | D (mm) | L (mm) | D (mm) | L (mm) | D (mm) | L (mm) | D (mm) | L (mm) | D (mm) | L (mm) | D (mm) | L (mm) | D (mm) | L (mm) |
| TGA | 14.50 | 38.13 | | | 10.91 | 34.00 | | | 8.58 | 27.60 | 7.85 | 29.38 | 8.19 | 38.20 |
| TLA | 20.27 | 47.26 | | | 13.85 | 35.94 | | | 8.23 | 26.45 | 7.98 | 24.05 | 8.49 | 38.30 |
| TPA | 19.75 | 46.38 | | | 12.22 | 39.95 | | | 9.44 | 29.29 | 8.57 | 29.80 | 9.04 | 44.10 |
| T-GLYC | | | 12.13 | 33.95 | 10.32 | 30.55 | 9.44 | 29.35 | 8.30 | 24.52 | 7.76 | 32.70 | | |
| CYSTM | 11.30 | 32.91 | | | 10.09 | 29.88 | | | 9.09 | 27.80 | 8.85 | 32.25 | 9.50 | 34.13 |
| GMTG | 11.24 | 32.85 | 9.98 | 29.43 | 10.27 | 29.24 | 11.83 | 32.97 | 13.10 | 34.36 | | | | |
| GMTL | 11.96 | 36.45 | 10.60 | 33.06 | 10.50 | 34.52 | 13.19 | 37.10 | 15.91 | 39.94 | | | | |
| GMTP | 13.41 | 37.69 | 13.21 | 36.00 | 11.13 | 34.05 | 10.02 | 31.43 | 7.76 | 30.80 | 7.55 | 32.79 | | |

TABLE III

Effect of pH of Hair Keratin Reducing Agent (HKRA) On Curl Tightness

| | pH | | | | | | | | | | | | | |
|---|---|---|---|---|---|---|---|---|---|---|---|---|---|---|
| | 7.0 | | 7.5 | | 8.0 | | 8.5 | | 9.0 | | 9.5 | | 10.0 | |
| HKRA | D (mm) | L (mm) | D (mm) | L (mm) | D (mm) | L (mm) | D (mm) | L (mm) | D (mm) | L (mm) | D (mm) | L (mm) | D (mm) | L (mm) |
| TGA | 14.28 | 35.74 | | | 10.53 | 30.48 | | | 8.49 | 26.25 | 8.54 | 35.95 | 9.40 | 40.16 |
| TLA | 17.25 | 46.58 | | | 11.82 | 35.08 | | | 8.75 | 28.18 | 8.12 | 31.35 | 9.10 | 43.75 |
| TPA | 16.40 | 42.79 | | | 11.07 | 35.20 | | | 8.80 | 27.37 | 8.50 | 39.81 | 8.97 | 49.19 |
| T-GLYC | | | 11.79 | 33.01 | 10.66 | 32.14 | 8.88 | 30.53 | 7.81 | 32.78 | 8.70 | 41.68 | | |
| CYSTM | 10.03 | 29.05 | | | 9.24 | 27.40 | | | 7.55 | 25.83 | 8.28 | 27.81 | 8.53 | 38.43 |
| GMTG | 9.23 | 26.37 | 9.66 | 29.76 | 10.49 | 32.50 | 11.68 | 33.15 | 13.37 | 36.55 | | | | |
| GMTL | 10.45 | 31.58 | 10.78 | 31.58 | 11.69 | 35.40 | 14.92 | 39.05 | 15.58 | 41.65 | | | | |
| GMTP | 13.26 | 38.03 | 11.12 | 35.28 | 10.58 | 32.95 | 9.43 | 29.44 | 7.80 | 29.94 | | | | |

TABLE IV

Deficiency in Wave Tightness (DIWT)
of Hair Keratin Reducing Agents (HKRA) vs. pH

| HKRA | pH | | | | | | |
|---|---|---|---|---|---|---|---|
| | 7.0 | 7.5 | 8.0 | 8.5 | 9.0 | 9.5 | 10.0 |
| TGA | 123 | | 68.0 | | 32.0 | 21.0 | 26.0 |
| TLA | 212 | | 113.0 | | 27.0 | 23.0 | 31.0 |
| TP | 204 | | 88.0 | | 45.0 | 32.0 | 39.0 |
| T-GLYC | | 87.0 | 59.0 | 45.0 | 28.0 | 19.0 | |
| CYSTM | 74 | | 55.0 | | 39.8 | 36.2 | 46.2 |
| GMTG | 73.0 | 50.0 | 58.0 | 79.0 | 101.0 | | |
| GMTL | 84.0 | 63.0 | 62.0 | 103.0 | 145.0 | | |
| GMTP | 104.0 | 106.0 | 59.0 | 47.0 | 28.0 | 16.0 | |

TABLE V

Deficiency in Wave Tightness (DIWT)
of Hair Keratin Reducing Agents (HKRA) vs. pH

| HKRA | pH | | | | | | |
|---|---|---|---|---|---|---|---|
| | 7.0 | 7.5 | 8.0 | 8.5 | 9.0 | 9.5 | 10.0 |
| TGA | 120 | | 62.0 | | 31.06 | 31.0 | 45.0 |
| TLA | 165 | | 82.0 | | 35.0 | 25.1 | 40.0 |
| TP | 152 | | 70.0 | | 35.0 | 31.0 | 38.0 |
| T-GLYC | | 81.4 | 64.0 | 36.6 | 20.2 | 33.8 | |
| CYSTM | 54.3 | | 42.2 | | 27.0 | 28.0 | 31.2 |
| GMTG | 42.0 | 43.0 | 61.0 | 80.0 | 106.0 | | |
| GMTL | 61.0 | 66.0 | 80.0 | 130.0 | 140.0 | | |
| GMTP | 104.0 | 71.0 | 63 | 45.0 | 20.0 | | |

As is evident from a review of Tables II-V, the reducing agents of the present invention are capable of providing enhanced permanent waving results at substantially higher pH levels than ordinarily employed for prior art reducing agents. In particular, glyceryl monothiopropionate is clearly demonstrated to provide superior results at pH levels ranging between about 8.0 and 9.5.

EXAMPLE 2

In order to further demonstrate the efficacy of employing the reducing agents of the present invention, additional tests were conducted to determine the tensile strength of the hair fibers after permanent waving with the present invention and prior art reducing agents. As is well known, the 20% index is a measure of the hair fiber damage in the yield region and is defined as the force ratio of treated to untreated hair fiber at 20% elongation. This method is commonly used to evaluate the damage being imparted to hair fibers.

In order to effectively measure the tensile strength of the hair, an Instron Apparatus Model 1120 was used with each of the samples detailed herein. In each test, the resistant forces for each of the hair fibers was determined at 20% elongation under aqueous immersion conditions. The overall results attained from these elongation tests are provided in Tables VI and VII. The values provided represent the initial reading (prior to treatment) minus the final reading (after treatment) divided by the initial reading. As a result, the values closest to 1.000 indicate stronger relative tensile properties.

In Table VI, the overall performance of glyceryl monothiopropionate as the sole reducing agent at different pH levels is provided. In performing these tests, the immersion method detailed above was employed with a 1.0N solution of glyceryl monothiopropionate being employed as the sole reducing agent, with its application being made at 37° C. for 10 minutes. In Table VI, the wave efficiency is shown by providing the resulting curl diameter (D) and length (L) for each pH level, while the overall damage to the hair fibers is provided by detailing the 20% index for each pH level.

In Table VII, the 20% index results obtained for each hair keratin reducing agent at different pH levels is provided. In testing each reducing agent, the immersion method detailed above was employed using a 1.0 solution of the reducing agent, applied at 37° C. for 10 minutes.

TABLE VI

Wave Efficiency (diameter and length) and Damage of
GMTP Waved Hair Fibers at Different pH

| pH* | Diameter (mm) | Length (mm) | 20% Index |
|---|---|---|---|
| 7.0 | 13.41 | 37.69 | 0.841 |
| 7.50 | 13.21 | 36.00 | 0.825 |
| 8.00 | 10.32 | 32.32 | 0.774 |
| 8.50 | 9.55 | 31.37 | 0.727 |
| 9.00 | 8.30 | 27.83 | 0.651 |
| 9.50 | 7.55 | 32.72 | 0.492 |

*pH adjusted using Ammonium Hydroxide

TABLE VII

20% Index of Waved Hair Fibers with
Hair Keratin Reducing Agents (HKRA) vs. pH

| HKRA | pH* | | | | | | |
|---|---|---|---|---|---|---|---|
| | 7.0 | 7.5 | 8.0 | 8.5 | 9.0 | 9.5 | 10.0 |
| TGA | 0.877 | | 0.827 | | 0.747 | 0.483 | 0.322 |
| TLA | 0.916 | | 0.809 | | 0.755 | 0.712 | 0.495 |
| TP | 0.849 | | 0.815 | | 0.730 | 0.542 | 0.232 |
| T-GLYC | | 0.859 | 0.830 | 0.794 | 0.659 | 0.423 | |
| CYSTM | 0.849 | | 0.810 | | 0.765 | 0.605 | 0.401 |
| GMTG | 0.836 | 0.814 | 0.833 | 0.859 | 0.900 | | |
| GMTL | 0.847 | 0.837 | 0.849 | 0.888 | 0.924 | | |
| GMTP | 0.841 | 0.825 | 0.774 | 0.727 | 0.651 | | |

*pH adjusted using Ammonium Hydroxide

EXAMPLE 3

In order to unequivocally demonstrate the ability of the reducing agents of the present invention to substantially reduce the malodor typically associated with permanent waving lotions, odor evaluations of reducing solutions employing the present invention were conducted using the "olfactory" methodology, as well as by quantitative measurement of the headspace for the presence of hydrogen sulfide. The quantitative analysis of hydrogen sulfide in the headspace was determined by pipetting 5.0 ml of the waving or reducing solution of the present invention into a 125 ml erlenmeyer flask, containing 20 ml water and 4 ml of 20% sulfuric acid.

The flask was sealed with parafilm and after 3 minutes at 37° C., headspace sampling was performed utilizing a hydrogen sulfide ($H_2S$) sensor tube manufactured by Matheson Gas Products. The amount of hydrogen sulfide measured was then recorded.

For purposes of comparison, the hydrogen sulfide content was also determined in the identical manner for conventional reducing hair keratin reducing agents. The comparative assay for hydrogen sulfide headspace content obtained from these tests are detailed in Table VIII.

Using a similar procedure as detailed above in reference to Table VIII, the hydrogen sulfide emission levels during hair reduction were determined for waving lotions of this invention and the prior art. The results of these tests are shown in Table IX.

TABLE VIII

Hydrogen Sulfide Emission Levels in Headspace of Waving Lotions

| Hair | PPM Hydrogen Sulfide* |
| --- | --- |
| Thioglycolic Acid | 120 |
| Thiolactic Acid | 34 |
| Thiopropionic Acid | 19 |
| Glyceryl Monothioglycolate | 6 |
| Glyceryl Thiolactate | 5 |
| Glyceryl Monothiopropionate | <0.1 |
| Thioglycerine | 8 |

*5 ml of 1.0N lotion at pH 9.0, using Ammonium Hydroxide + 20 ml Water + 5 ml of 20% Sulfuric Acid

TABLE IX

Headspace Hydrogen Sulfide Emission Levels During Hair Reduction

| MERCAPTAN | PPM Hydrogen Sulfide* |
| --- | --- |
| Thioglycolic Acid | 175 |
| Thiolactic Acid | 43 |
| Thiopropionic Acid | 40 |
| Glyceryl Monothioglycolate | 85 |
| Glyceryl Thiolactate | 124 |
| Glyceryl Monothiopropionate | 24 |
| Thioglycerine | 32 |

*0.5 g of hair + 10 ml of 1.0N lotion at pH 9.0, using Ammonium Hydroxide

As detailed in Tables VIII and IX, the reducing agents of the present invention, particularly glyceryl monothiopropionate, release substantially smaller amounts of hydrogen sulfide than the conventional, prior art reducing agents. Furthermore, the reducing agents of this invention were found to exhibit a very low odor during processing and reduction of hair keratin, while also subsequently yielding virtually no post perm odor.

EXAMPLE 4

In order to confirm the reducing efficiency or permanent wave setting of hair fibers attainable with the reducing agents of the present invention in comparison to prior art reducing agents, an amino acid analysis was conducted using the excess lotion or immersion method.

In conducting these tests, the hair fibers were first shampooed and then immersed in one of the permanent waving lotions. Unless otherwise specified, the tests were conducted using a permanent wave lotion incorporating a 1.0N aqueous solution of the reducing agent, applied for ten minutes at 37° C.

After ten minutes of exposure, the hair fibers were endcapped with iodoacetic acid/sodium iodoacetate mixtures. The treated hair fibers were then hydrolyzed with 6N HCl for 24 hours, employing the method disclosed by S. Moore and W. H. Stein in *Methods Enzymol*, 6 (1963) Page 819.

The amino acid analysis resulting from the hair hydrolyzates for each of the reducing agents at various pH levels are detailed in Table X. As is evident from these results, the reducing agents of the present invention are effective in achieving the required S—S cleavage for providing a long lasting, permanent wave.

TABLE X

Comparative Hair S—S Cleavage of Reducing Agents

| Reducing Agent | % S—S Cleavage | pH* |
| --- | --- | --- |
| TGA | 79.1 | 9.5 |
| TLA | 76.2 | 9.5 |
| TPA | 69.3 | 9.5 |
| CYSTM | 31.1 | 9.0 |
| T-GLYC | 58.7 | 9.0 |
| GMTG | 45.7 | 7.8 |
| GMTL | 32.0 | 7.8 |
| GMTP | 78.2 | 9.1 |

*pH was adjusted with Ammonium Hydroxide

As is evident from a review of the test results detailed in Tables II–X, the reducing agents of the present invention provide a unique balance at higher pH levels of effectively permanently waving hair fibers, while minimizing the damage to the hair fibers and substantially eliminating the malodor typically associated with permanent waving of hair. In particular, the use of glyceryl monothiopropionate, in accordance with the present invention, achieves substantially enhanced, long-lasting permanent waving of hair fibers with minimal damage being caused to the hair fibers while the malodor is virtually eliminated. In particular, these benefits are attained by glyceryl monothiopropionate at pH levels ranging between about 8.0 and 9.5.

It will thus be seen that the objects set forth above, among those made apparent from the preceding description, are efficiently attained and, since certain changes may be made in carrying out the above process and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A hair reducing or permanent waving lotion for use in the permanent waving of hair, said lotion comprising A. between about 5% and 50% by weight of the total composition of a reducing agent selected from the group consisting essentially of glyceryl monothiopropionate, glyceryl thiolactate, and combinations of glyceryl monothiopropionate and glyceryl thiolactate whereby said selected reducing agent comprises the sole reducing agent in said lotion;

B. between about 2% and 6% by weight of an ionic or non-ionic detergent;

C. between about 1% and 3% by weight of ammonium chloride;

D. between about 2% and 5% by weight of a penetrating agent; and

E. one or more agents selected from the group consisting of protein hydrolyzates, chelating agents, wetting agents, fragrances, conditioning agents and water.

2. The permanent waving lotion defined in claim 1, wherein said lotion is further defined as comprising an alkaline agent selected from the group consisting of ammonia, ammonium hydroxide, monoethanolamine, guanidine, diethanolamine, triethanolamine, ammonium carbonate, and bicarbonate in sufficient amount to adjust the pH of the lotion to a range between about 6.0 and 9.5.

3. The permanent waving lotion defined in claim 2, wherein the penetrating agent is further defined as comprising one selected from the group consisting of phenoxyethanol, urea, 2,3 hexanediol and phytantriol.

4. The permanent waving lotion defined in claim 2, and further comprising an oxidizing agent selected from the group consisting of hydrogen peroxide and water soluble salts of bromates, for producing an exothermic reaction.

5. A hair reducing or permanent waving lotion for use in the permanent waving of hair, said lotion comprising
   A. between about 5% and 50% by weight of the total composition of a reducing agent comprising glyceryl monothiopropionate;
   B. between about 2% and 6% by weight of an ionic or non-ionic detergent;
   C. between about 1% and 3% by weight of ammonium chloride;
   D. between about 2% and 5% by weight of a penetrating agent;
   E. one or more agents selected from the group consisting of protein hydrolyzates, chelating agents, wetting agents, fragrances, conditioning agents and water; and
   F. a pH level ranging between 8.0 and 9.2.

6. A process for providing enhanced permanent waving of hair with substantially less malodor being produced, said process comprising the steps of
   A. forming a permanent waving lotion comprising
      a. a reducing agent consisting essentially of between about 5% and 50% by weight of the total lotion composition, said reducing agent being selected from the group consisting essentially of glyceryl monothiopropionate, glyceryl thiolactate, and combinations of glyceryl monothiopropionate and glyceryl thiolactate, whereby said selected reducing agent comprises the sole reducing agent in said lotion;
      b. between about 2% and 6% by weight of the total composition of an ionic or non-ionic detergent,
      c. between about 1% and 3% by weight of the total composition of ammonium chloride,
      d. between about 2% and 5% by weight of the total composition of a penetrating agent, and
      e. water forming the balance;
   B. moistening hair to be permanently waved;
   C. rolling the moistened hair fibers onto curlers for securement thereto;
   D. applying the permanent waving lotion to the rolled hair fibers;
   E. allowing the permanent waving lotion to remain on the hair for between about 10 and 60 minutes;
   F. rinsing the hair with water and blotting to remove excess moisture; and
   G. neutralizing or oxidizing the hair by employing a solution comprising one or more agents selected from the group consisting of acidic hydrogen peroxide, alkaline bromate, and sodium chloride.

7. The process defined in claim 6, wherein the neutralizing or oxidizing solution further comprises a water soluble salt selected from the group consisting of sulfites and bisulfites to provide an exothermic reaction.

8. The process defined in claim 6, wherein said permanent waving lotion is further defined as comprising an alkaline agent selected from the group consisting of ammonia, ammonium hydroxide, monoethanolamine, guanidine, diethanolamine, triethanolamine, ammonium carbonate, and bicarbonate in sufficient amount to adjust the pH of the permanent waving lotion to range between about 6.0 and 9.5.

9. The process defined in claim 8, wherein said permanent wave lotion is further defined as comprising an oxidizing agent selected from the group consisting of hydrogen peroxide and water soluble salts of bromates, for producing an exothermic reaction.

10. The process defined in claim 8, comprising the additional step of
    H. heating the hair during the processing of the permanent waving lotion.

11. The process defined in claim 10, wherein said hair is heated to a temperature of about 50° C.

12. The process defined in claim 8, wherein the permanent waving lotion is further defined as being prepared by intermixing all of the ingredients except the reducing agent and intermixing the reducing agent with the previously intermixed ingredients immediately prior to applying the permanent waving lotion to the head of hair to be permanently waved.

13. The process defined in claim 12, wherein the permanent waving lotion is further defined as being prepared by separately intermixing the reducing agent with the alkaline agent, and said alkaline agent comprises a quantity sufficient to enable the pH level of the permanent waving lotion to range between about 6.0 and 9.5.

14. The process defined in claim 13, wherein the permanent waving lotion is further defined as comprising an oxidizing agent selected from the group consisting of hydrogen peroxide and water soluble salts of bromates, said oxidizing agent being prepared separately and added to the permanent waving lotion immediately prior to use, thereby causing an exothermic reaction to occur.

15. A process for providing enhanced permanent waving of hair with substantially less malodor being produced, said process comprising the steps of
    A. forming a permanent waving lotion comprising
       a. a reducing agent consisting essentially of between about 5% and 50% by weight of the total composition said reducing agent comprising glyceryl monothiopropionate;
       b. between about 2% and 6% by weight of the total composition of an ionic or non-ionic detergent,
       c. between about 1% and 3% by weight of the total composition of ammonium chloride,
       d. between about 2% and 5% by weight of the total composition of a penetrating agent, and
       e. water forming the balance, and
       f. a pH level ranging between about 8.0 and 9.2;
    B. moistening hair to be permanently waved;
    C. rolling the moistened hair fibers onto curlers for securement thereto;
    D. applying the permanent waving lotion to the rolled hair fibers;
    E. allowing the permanent waving lotion to remain on the hair for between about 10 and 60 minutes;
    F. rinsing the hair with water and blotting to remove excess moisture; and
    G. neutralizing or oxidizing the hair by employing a solution comprising one or more agents selected from the group consisting of acidic hydrogen peroxide, alkaline bromate, and sodium chloride.

* * * * *